(12) United States Patent
Dusterhoft et al.

(10) Patent No.: US 12,403,014 B2
(45) Date of Patent: Sep. 2, 2025

(54) VARIABLE LORDOSIS ENDPLATE

(71) Applicant: Astura Medical Inc., Iriving, TX (US)

(72) Inventors: Ross Dusterhoft, Irving, TX (US);
Thomas Purcell, Irving, TX (US)

(73) Assignee: Astura Medical Inc., Irving, TX (US)

( * ) Notice: Subject to any disclaimer, the term of this patent is extended or adjusted under 35 U.S.C. 154(b) by 142 days.

(21) Appl. No.: 18/378,629

(22) Filed: Oct. 10, 2023

(65) Prior Publication Data
US 2024/0138996 A1     May 2, 2024

Related U.S. Application Data

(60) Provisional application No. 63/414,814, filed on Oct. 10, 2022.

(51) Int. Cl.
    *A61F 2/44*     (2006.01)

(52) U.S. Cl.
    CPC ...... *A61F 2/4425* (2013.01); *A61F 2002/443* (2013.01); *A61F 2250/0006* (2013.01)

(58) Field of Classification Search
    CPC .................................................. A61B 17/4425
    See application file for complete search history.

(56) References Cited

U.S. PATENT DOCUMENTS

2021/0401586 A1*   12/2021   Zakelj ................... A61F 2/4455

* cited by examiner

*Primary Examiner* — Olivia C Chang
(74) *Attorney, Agent, or Firm* — Michael R. Shavin

(57) ABSTRACT

A variable lordosis endplate that may adjusted from 0 to 30 degrees using a mechanical drive that allows the spine's angle to be physically adjusted in-situ. The variable lordosis endplate may be quickly attached to either end, or both ends, of the central column. The variable lordosis endplate can be attached in orientations of every 15 degrees. The variable lordosis endplates' lordotic angles may be on either end of the column independently from one another. By attaching a variable lordosis endplate to both ends of the column, hyper-lordotic angles may be achieved.

14 Claims, 7 Drawing Sheets

VARIABLE LORDOSIS ENDPLATE

CROSS-REFERENCE TO RELATED APPLICATIONS

This application claims the benefit of U.S. Provisional Application No. 62/414,814 filed Oct. 10, 2022, which is incorporated herein by reference.

FIELD

The present invention relates generally to the field of spinal surgery, and more specifically, to a vertebral body replacement having a variable lordosis endplate.

BACKGROUND

A spinal disc can become damaged as a result of degeneration, dysfunction, disease and/or trauma. Conservative treatment can include non-operative treatment through exercise and/or pain relievers to deal with the pain. In surgical treatments, interbody spacers may be used between adjacent vertebra, resulting in spinal fusion of the adjacent vertebra. Treatment options include disc removal and replacement using an interbody spacer, such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

The current standard of care for interbody fusion requires surgical removal of all or a portion of the intervertebral disc. After removal of the intervertebral disc, the interbody spacer is inserted into the intervertebral space to occupy the intervertebral space after the disc is removed. This requires that an opening sufficient to allow the interbody spacer must be created through surrounding tissue to permit the interbody spacer to be inserted into the intervertebral space.

In some cases, the interbody spacer may be required to change or correct the lordosis angle of the intervertebral space. Current systems offer a large selection of implants of varying lordosis and footprint options to meet specific patient anatomy requirements. This large selection of implants dramatically increases the amount of required inventory required by the implant manufacturer.

It would be desirable to have a variable lordosis implant that can have its lordosis dynamically adjusted to meet any patient's lordosis requirement.

SUMMARY OF THE INVENTION

Embodiments of the present invention are directed to a variable lordosis endplate that may be quickly attached to either end (or both ends) of the central column. The variable lordosis endplate can be attached in orientations of every 15 degrees. The variable lordosis endplates' lordotic angles may be adjusted in-situ from 0 to 30 degrees on either end of the column independently from one another. The variable lordosis endplate has a drive mechanism, such as a mechanical drive, that allows the spine's angle to be physically adjusted. By attaching a variable lordosis endplate to both ends of the column, hyper-lordotic angles may be achieved. One or both of the variable lordosis endplates may be removed from the central column if desired.

Further embodiments, features, objects and advantages of the invention, as well as structure and operation of various embodiments of the invention, are disclosed in detail below with references to the accompanying drawings. There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE DRAWINGS

The present embodiments may be understood from the following detailed description when read in conjunction with the accompanying figures. It is emphasized that the various features of the figures are not necessarily to scale. On the contrary, the dimensions of the various features may be arbitrarily expanded or reduced for clarity.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Broadly, the present invention provides a variable lordosis endplate that may be quickly attached to either end (or both ends) of the central corpectomy column. The variable lordosis endplate can be attached in orientations of every 15 degrees. The variable lordosis endplates' lordotic angles may be adjusted in-situ from 0 to 30 degrees on either end of the column independently from one another. The variable lordosis endplate has mechanical drive that allows the spine's angle to be physically adjusted. By attaching a variable lordosis endplate to both ends of the column, hyper-lordotic angles may be achieved. One or both of the variable lordosis endplates may be removed from the central column if desired. The variable lordosis endplate described herein may be cervical, thoracic or lumbar variable lordosis plates.

The present invention provides a variable lordosis endplate that utilizes a novel mechanical lordosis adjustment mechanism that includes a drive mechanism to translate a shuttle perpendicular to the longitudinal axis of the central column. The endplate only rotates about a posterior hinge pin and relies on the adjustment mechanism for height adjustment. The posterior hinge pin is offset from the column' central, longitudinal axis. Anterior shuttle pins are in double mechanical shear while the posterior hinge pin is in quadruple mechanical shear, increasing the strength of the mechanism and causing the shuttle to assume an abstract profile. As the shuttle translates, it encapsulates the portion of the body that houses the driver. This increases the torsional strength of the assembly. The invention features quick-connect modularity to either end of the central column.

Figure 1A:
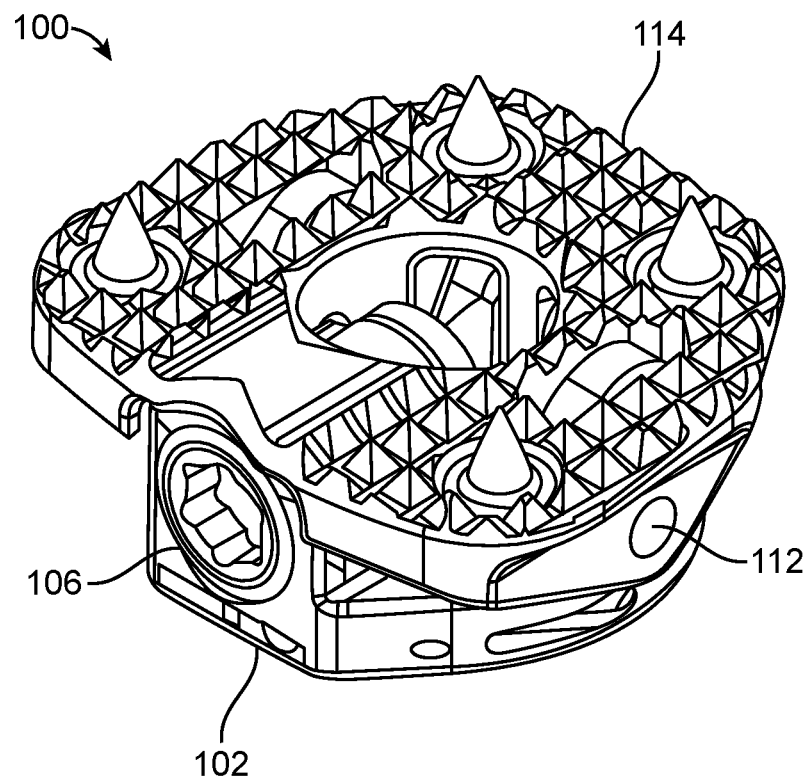
FIGS. 1A, 1B are a perspective view and a side view showing one embodiment of variable lordosis endplate in a collapsed state.
Figure 1B:
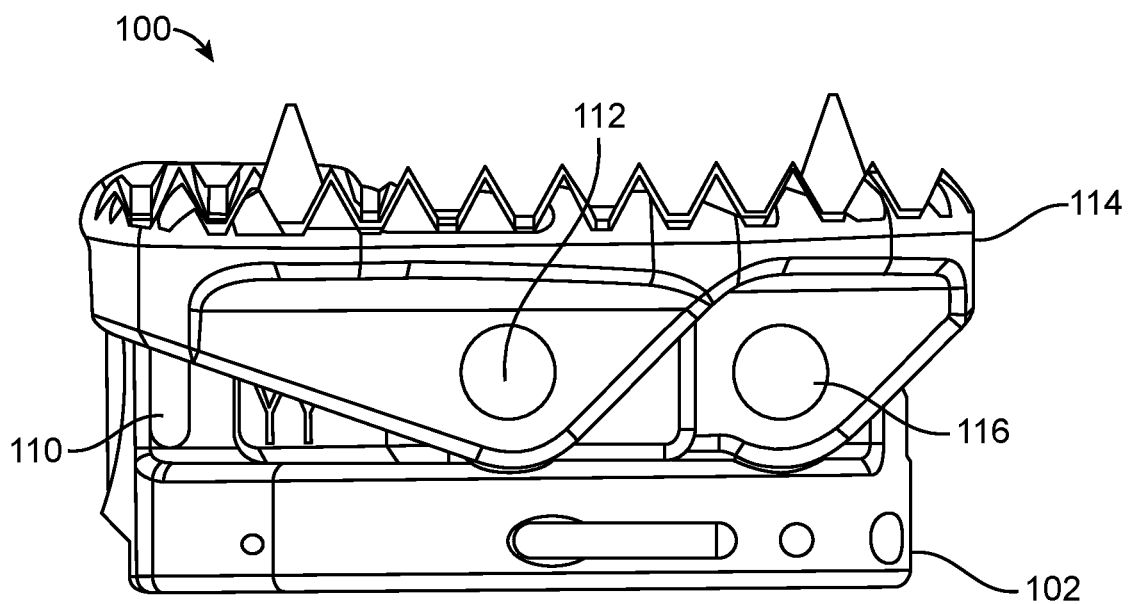

FIGS. 1A, 1B show a perspective view and a side view of one embodiment of variable lordosis endplate 100 in a collapsed state. A preassembled lordosis endplate 100 is designed to be quickly attached to either end, or both ends, of a central column. The variable lordosis endplate 100 can be attached in orientations of every 15 degrees. Attaching the variable lordosis endplate 100 to both ends of the column, hyper-lordotic angles may be achieved. One or both of the endplates may be removed from the central column if desired. The variable lordosis endplate 100 has mechanical drive 106 that allows the spine's angle to be physically adjusted.

The variable lordosis endplate 100 includes a lower endplate or body 102 rotatably coupled to an upper endplate 114 with a hinge pin 116. A driver 106 is rotationally coupled to the body 102. A shuttle 110 is coupled to the driver 106 and slidingly coupled to the upper endplate 114 with a shuttle pin 112.

Figure 2A:
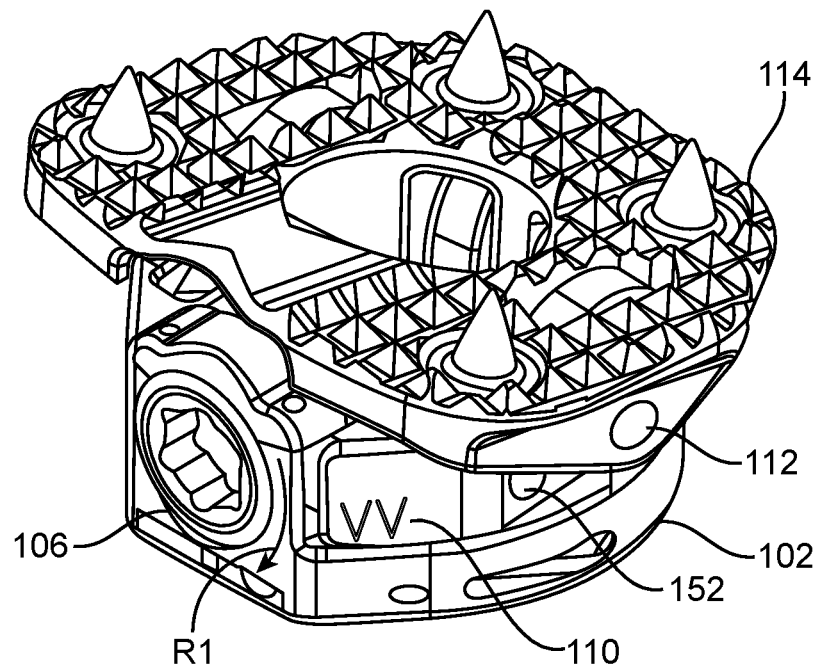
FIGS. 2A, 2B are a perspective view and a side view showing the variable lordosis endplate in an expanded state.
Figure 2B:
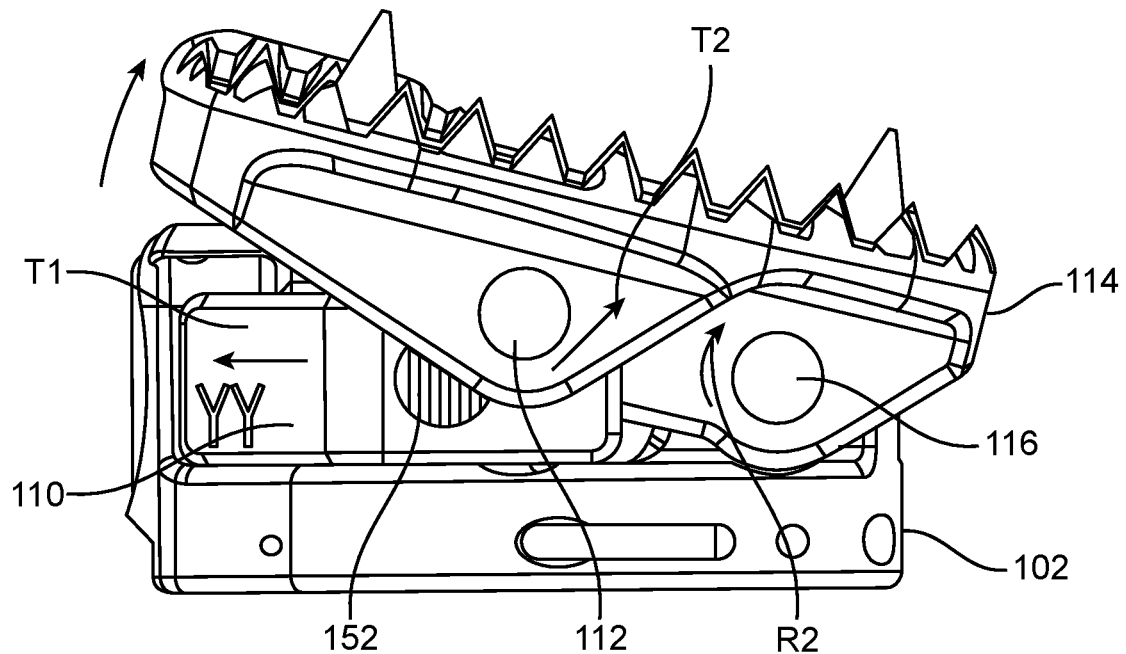

FIGS. 2A, 2B show a perspective view and a side view of the variable lordosis endplate 100 in an expanded state. Rotation of the driver 106 is configured to move the shuttle proximally or distally T1 to lift or lower the proximal portion of the upper endplate 114 away from the lower endplate 102 to change the lordotic angle. The lordotic angle of the upper endplate 114 may be adjusted from 0 to 30 degrees, either before implantation or in-situ by the surgeon. The lordotic angle of the upper endplate 114 may be any angle between the collapsed state, 0 degrees, and the expanded state, 30 degrees.

To expand the variable lordosis endplate 100 from the collapsed state to expanded state, the driver 106 is rotated R1 so that the shuttle 110 translates T1 proximally along a threaded portion of the driver 106. As the shuttle 106 translates, the shuttle pins 112 translate T2 or slide in angled slots 152, rotating R2 the upper endplate 114 on the hinge pin 116. The rotation on the hinge pin 116 raises the proximal end of the upper endplate 114 away from the proximal end of the body 102, thereby changing the lordotic angle of the upper endplate 114.

Figure 3A:
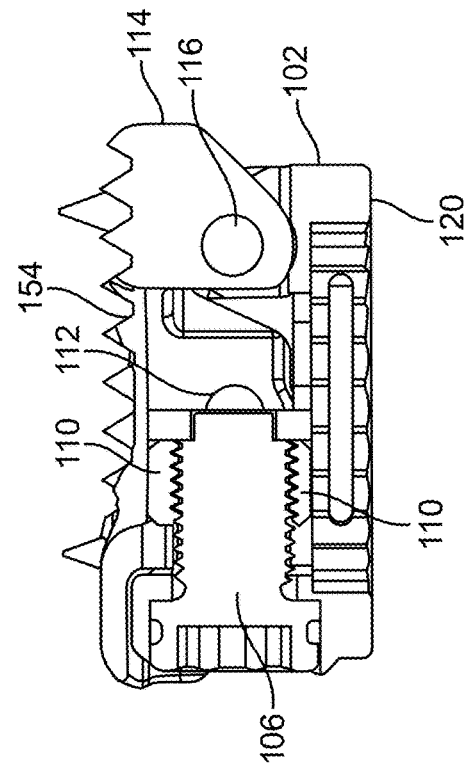
FIGS. 3A, 3B show a front view and a sectional view of the variable lordosis endplate in the collapsed state.
Figure 3B:
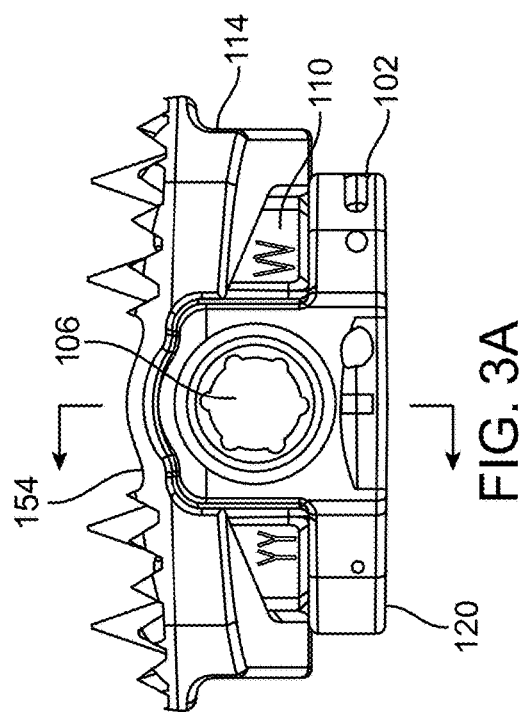

FIGS. 3A, 3B show a front view and a sectional view of the variable lordosis endplate 100 in the collapsed state. In the collapsed state, a top surface 154 of the upper endplate 114 and a bottom surface 120 of the body 102 are parallel to each other. The proximal end of the driver 116 includes a tool engagement feature configured to engage a driver actuation tool to rotate the driver 116. In the collapsed state, the shuttle 110 is positioned near a distal end of the threaded portion of the driver 100.

Figure 4A:
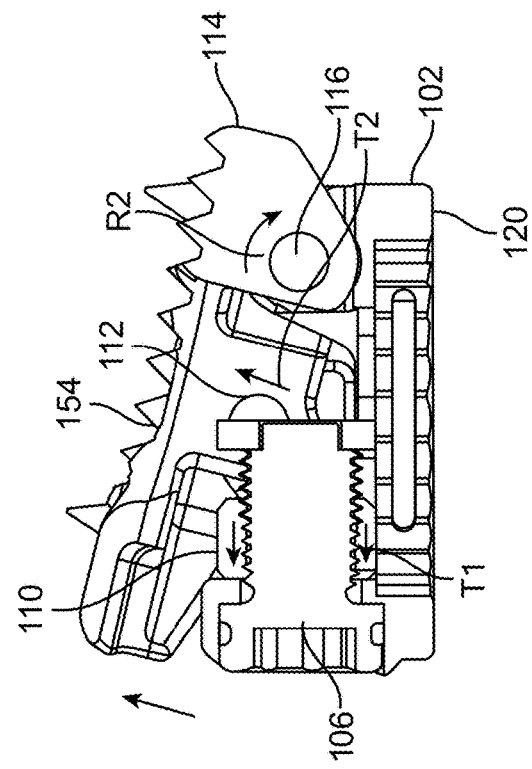
FIGS. 4A, 4B show a front view and a sectional view of the variable lordosis endplate in the expanded state.
Figure 4B:
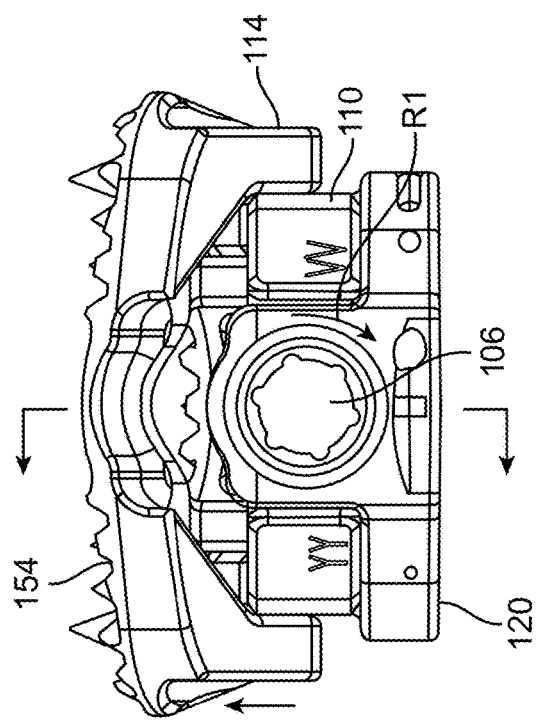

FIGS. 4A, 4B show a front view and a sectional view of the variable lordosis endplate 100 in the expanded state. To expand the variable lordosis endplate 100 from the collapsed state to expanded state, a driver actuation tool is used to rotate R1 the driver 106 and translate T1 the shuttle 110 from the distal end of the threaded portion of the driver 106 toward the proximal end. In the expanded state, the top surface 154 of the upper endplate 114 is angled at a lordotic angle in relation to the bottom surface 120 of the body 102. The lordotic angle may be adjusted to any angle between 0 to 30 degrees. In other embodiments, the angle may be greater than 30 degrees.

Figure 5:
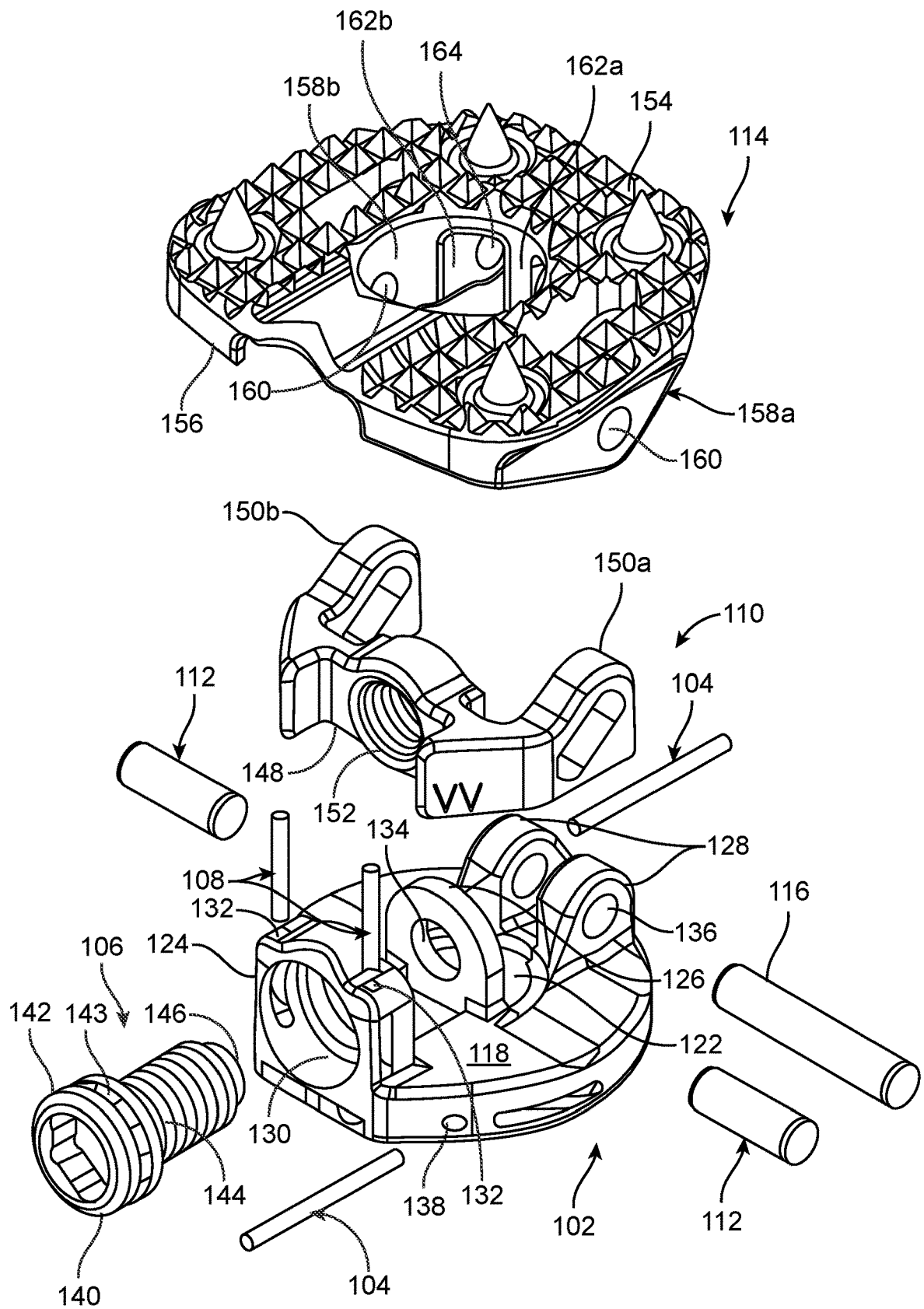
FIG. 5 is an exploded perspective view showing of the variable lordosis endplate.

FIG. 5 shows an exploded perspective side view of a variable lordosis endplate 100 having a body 102, column quick attachment pins 104, a driver 106, driver retention pins 108, a shuttle 110, shuttle pins 112, an upper endplate 114, and a hinge pin 116.

The body 102 includes an upper surface 118, a lower surface 120, and a central opening 122. The upper surface 118 includes a proximal driver holder 124, a distal driver holder 126, and one or more hinge pin holders 128. The proximal driver holder 124 includes a driver head opening 130 and one or more driver retention pin holes 132 configured to receive the driver retention pins 108. The distal driver holder 126 includes a driver shaft opening 134. The one or more hinge pin holders 128 include a hinge pin hole 136 configured to receive the hinge pin 116. The body 102 also includes one or more column attachment pin holes 138 configured to receive the column attachment pins 104. The column attachment pins 104 are made of a flexible wire that is configured to flex and click into grooves within a central column.

The variable lordosis endplate 100 is movable between a collapsed state (shown in FIG. 1A) to an expanded state (shown in FIG. 2A) via proximal movement of the shuttle 110 by the driver 106. In the embodiment shown, the driver 106 is a drive screw that includes a proximal end having a driver head 140 with a retention groove 142 and threaded shaft 144 with a distal end 146. The driver head 140 is sized to fit within the driver head opening 130 and the retention pins 108 retain the driver to the body while preventing the driver from rotating when the plate is compressed. The flexible pins rest on flats 143 within the driver to resist rotation forces generated through the driver's thread. The retention pins 108 may be flexible nitinol wires. Other forms of driver retention may be used to the same effect such as a flexible retaining ring. The distal end 146 of the threaded shaft 144 is configured to rotatably couple with the driver shaft opening 134.

In the embodiment shown, the shuttle 110 has a generally U-shape with a proximal frame 148 and arms 150a, 150b extending distally from the frame 148. The proximal frame 148 includes a threaded hole 152 configured to rotatably couple with the threaded shaft 144 of the driver 106. The arms 150a, 150b include angled slots 152a, 152b configured to receive the shuttle pins 112.

Rotation of the driver 106 axially translates the shuttle 110 on the threads 144. Rotation of the driver 106 in a first direction translates the shuttle 110 proximally and rotation of the driver 106 in a second direction translates the shuttle 110 distally. Simultaneously as the shuttle 110 translates, the shuttle pins 116a, 116b translate up or down in the angled slots 152a, 152b lifting or lowering the proximal portion of the upper endplate to change the lordotic angle of the variable lordosis endplate 100.

The upper endplate 114 includes an upper surface 154 and a lower surface 156. The upper surface 154 is configured to contact a vertebra. The lower surface includes shuttle pin holders 158a, 158b with shuttle pin holes 160, and one or more hinge pin holders 162a with hinge pin holes. The upper endplate 114 may vary in shape and/or geometry for the different spinal locations and/or anatomical needs.

Figure 6A:
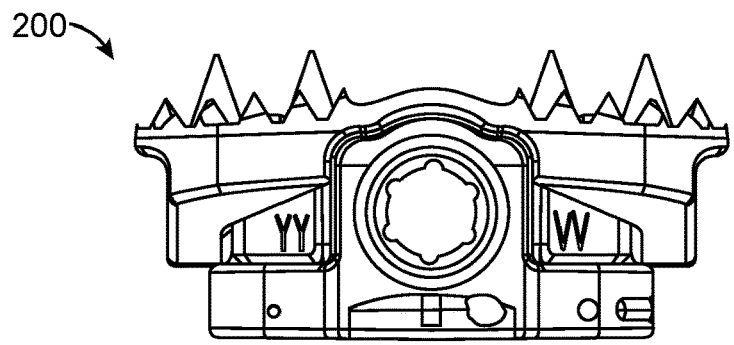
FIGS. 6A-6C show an embodiment of a cervical variable lordosis endplate showing a front view and a perspective view of the variable lordosis endplate in a collapsed state and a perspective view showing the variable lordosis endplate in an expanded state.
Figure 6B:
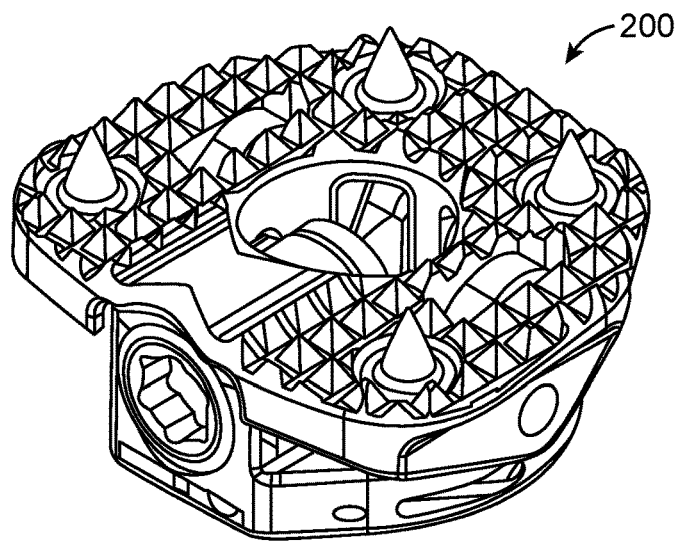
Figure 6C:
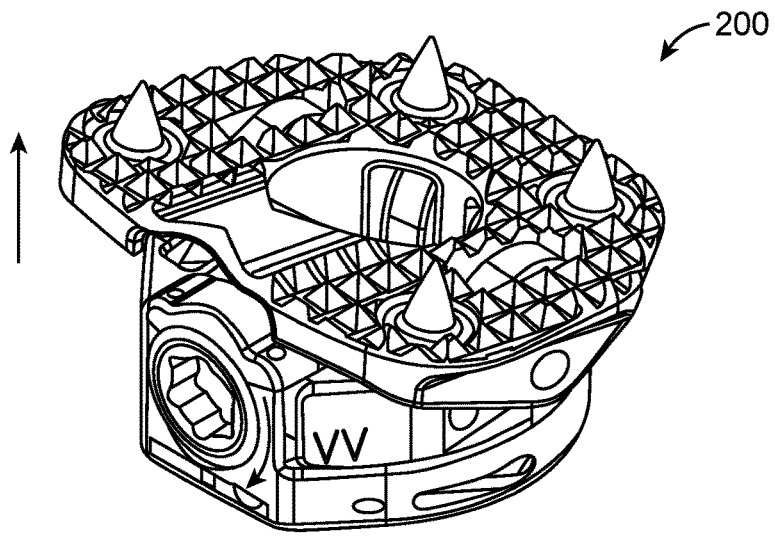

FIGS. 6A-6C show a front view and perspective view of a variable lordosis endplate 200 in a collapsed state and a perspective view showing the variable lordosis endplate 200 in an expanded state. The variable lordosis endplate 200 shown is designed for use in a cervical application.

Figure 7A:
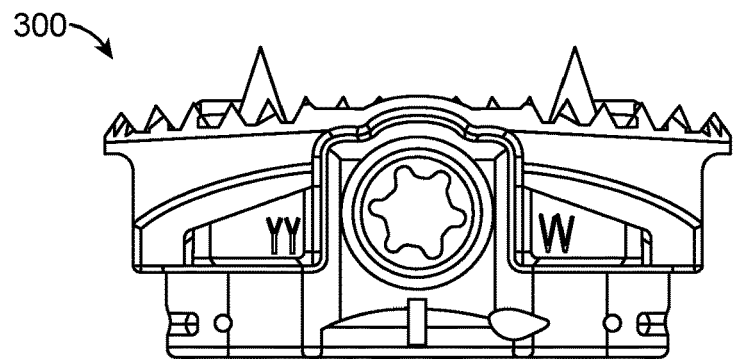
FIGS. 7A-7C show an embodiment of a thoracic variable lordosis endplate showing a front view and a perspective view of the variable lordosis endplate in a collapsed state and a perspective view showing the variable lordosis endplate in an expanded state. The thoracic variable lordosis endplate includes an upper endplate that is round and larger than the cervical upper endplate.
Figure 7B:
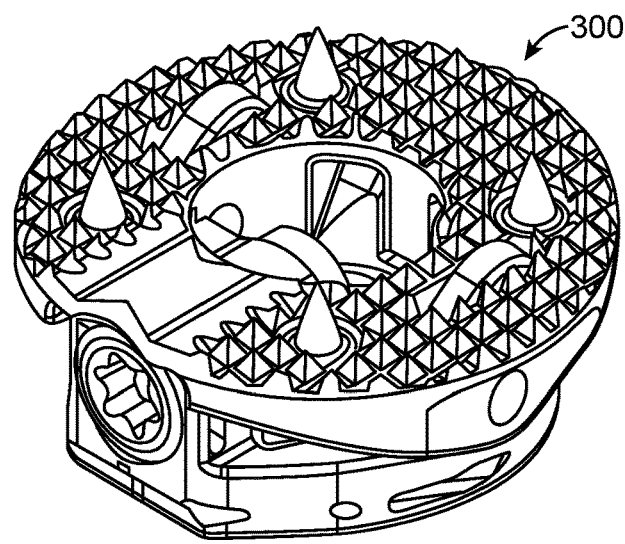
Figure 7C:
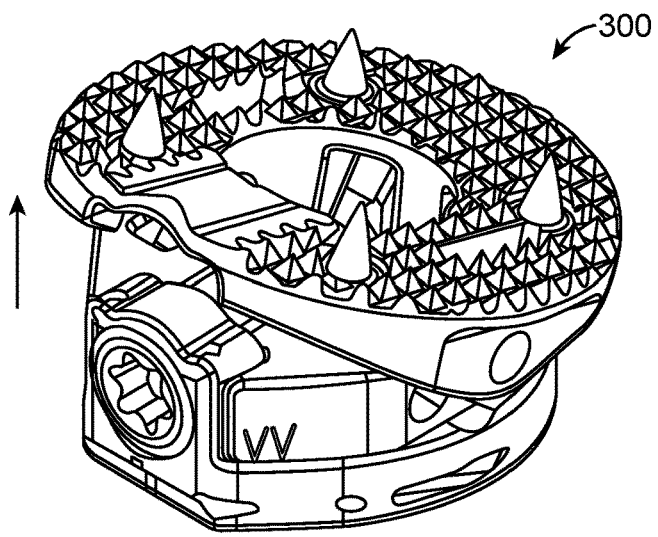

FIGS. 7A-7C is a front view and perspective view showing a variable lordosis endplate 300 in a collapsed state and a perspective view showing the variable lordosis endplate 300 in an expanded state. The variable lordosis endplate 300 shown is designed for use in a thoracic application having an upper endplate that is round and larger than the cervical upper endplate.

Figure 8A:
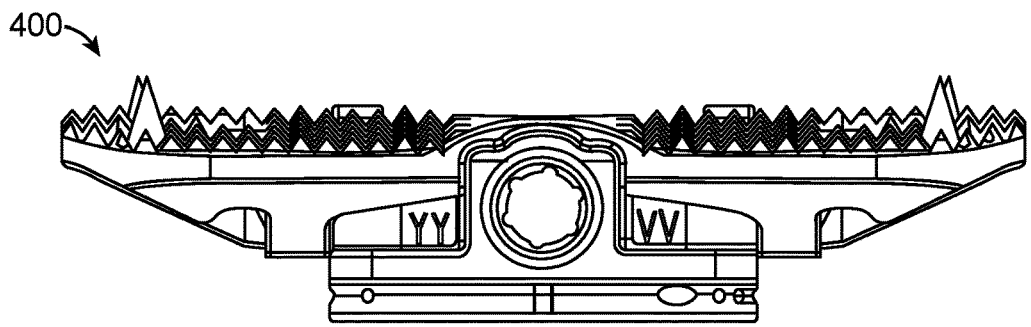
FIGS. 8A-8C show an embodiment of a lumbar variable lordosis endplate showing a front view and a perspective view of the variable lordosis endplate in a collapsed state and a perspective view showing the variable lordosis endplate in an expanded state. The lumbar variable lordosis endplate shown includes an upper endplate that is rectangular and larger than the cervical or thoracic endplate.
Figure 8B:
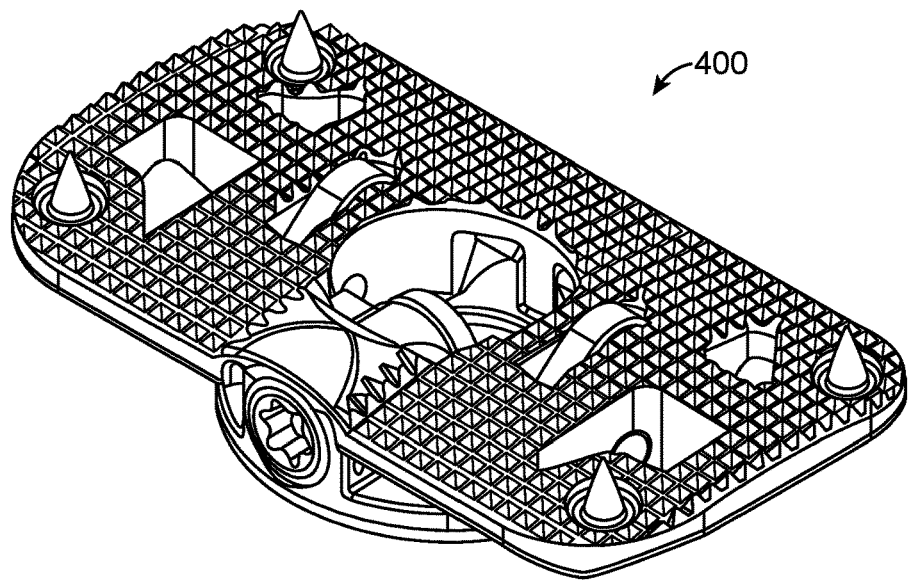
Figure 8C:
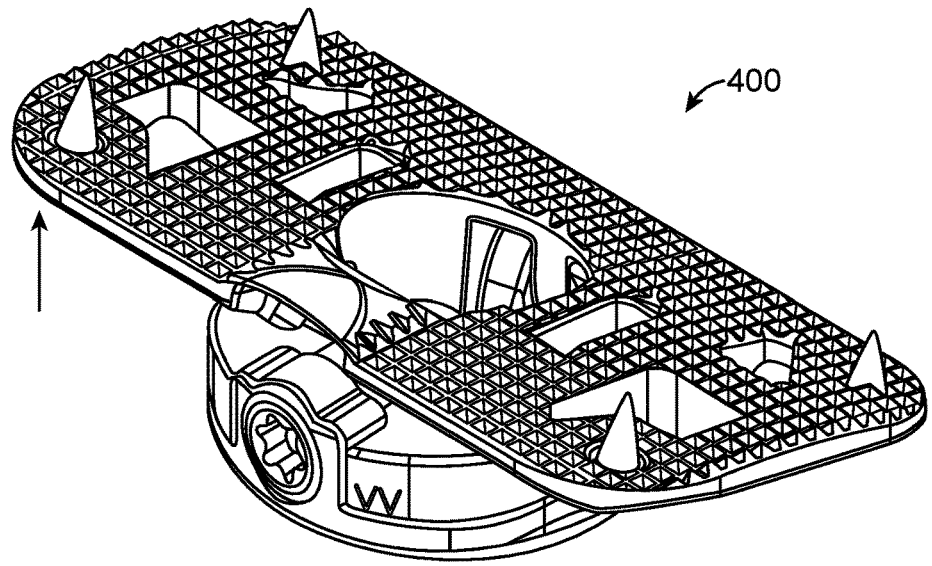

FIGS. 8A-8C is a front view and perspective view showing a variable lordosis endplate 400 in a collapsed state and a perspective view showing the variable lordosis endplate 400 in an expanded state. The variable lordosis endplate 400 shown is designed for use in a lumbar application having an upper endplate that is rectangular and larger than the cervical or thoracic endplate.

While a driver 106 is shown, any suitable mechanism may be used that is capable of translating the shuttle 110 proximally or distally to rotate the upper endplate 114 to change the lordotic angle.

The variable lordosis endplate 100 is movable between a collapsed state (shown in FIG. 1A) to an expanded state (shown in FIG. 2A) via movement of the shuttle 110 by the driver 106. In the embodiment shown, the shuttle 110 is positioned near the distal end of the driver 106. Rotation of the driver 106 in a first direction R1 proximally translates T1 the shuttle 110. Simultaneously, the shuttle pins 116a, 116b are translated T2 upwardly in the angled slots 152a, 152b to rotate the upper endplate 114 around the hinge pin 116 in a first direction R2 to increase the lordotic angle.

Rotation of the driver 106 in a second direction translates the shuttle 110 distally. Simultaneously, the shuttle pins 116a, 116b are translated downwardly in the angled slots 152a, 152b to rotate the upper endplate 114 around the hinge pin 116 in a second direction to lower the lordotic angle.

All components may be comprised of machined, anodized titanium expect for the nitinol pins which consist of super elastic nitinol.

The lordotic angle adjustment of the variable lordosis endplate 100 may be performed when the variable lordosis endplate 100 is coupled to the patient's spine. Thus, a surgeon can install the variable lordosis endplate 100 into the patient' spine and then rotate and rotate the driver to change the lordotic angle in-situ. Thus, prior to installation, the variable lordosis endplate 100 may be preassembled with a first lordotic angle, but once it is installed, the lordotic angle may be adjusted by the surgeon to a second lordotic angle.

The improvements made by the present invention include:
The variable lordosis endplate only requires inventory of varying footprints since the lordotic profile can be adjusted across a wide range (0 to 30 degrees per endplate).
New flexibility is achieved in the operating room by having the option of one or two variable lordosis endplates.
The endplates may be removed in the operating room to facilitate different surgical techniques if needed.
The surgeon may fine-tune the implant's lordotic profile in-situ instead of having to choose between pre-set angles. Prior art systems inserted with endplates of an undesirable lordotic angle would then have to be removed have the endplates changed.

While embodiments and applications of this invention have been shown and described, it would be apparent to those skilled in the art that many more modifications than mentioned above are possible without departing from the inventive concepts herein.

The invention claimed is:

1. A variable lordosis endplate comprising:
a body having a body upper surface;
a driver coupled to the body upper surface;
an upper endplate having an endplate lower surface hingedly coupled to the body upper surface;
a shuttle having a first part coupled to the driver for axial translation and a second part coupled to the upper endplate lower surface for lifting translation, wherein the driver includes a threaded portion coupled to the first part of the shuttle, and rotation of the driver axially translates the shuttle;
wherein the driver is configured to simultaneously translate the shuttle axially and lift the upper endplate angularly away from the body to change a lordosis angle;
wherein the second part of the shuttle includes angled slots coupled to the upper endplate with a shuttle pin, during axial translation of the shuttle on the threaded portion of the driver, the shuttle pin translates up the angled slots to lift the proximal end of the upper endplate away from the body to change the lordosis angle.

2. The variable lordosis endplate of claim 1, wherein the driver is configured to translate the shuttle from a first position with no lordosis angle to a second position with a lordosis angle.

3. The variable lordosis endplate of claim 2, wherein in the first position the variable lordosis endplate is in a collapsed state with an upper endplate surface being parallel to a lower body surface.

4. The variable lordosis endplate of claim 2, wherein in the second position the variable lordosis endplate is in an expanded state with a lordosis angle between the upper endplate and the lower body surface.

5. The variable lordosis endplate of claim 2, wherein the lordosis angle is variable by stopping the translation of the shuttle anywhere between the first and second positions.

6. The variable lordosis endplate of claim 1, wherein the lordosis angle is between 0 to 30 degrees.

7. A variable lordosis endplate comprising:
an upper endplate having an upper surface and a lower surface with upper hinge pin holders;
a lower endplate having a lower surface and an upper surface with lower hinge pin holders;
a hinge pin rotatably coupled to the upper and lower hinge pin holders;

a driver rotatably coupled to the lower endplate;

a shuttle axially coupled to the driver and angularly coupled to the upper endplate, the driver being configured to move the shuttle from a first position to a second position to change to a lordosis angle between the upper surface of the upper endplate and the lower surface of the lower endplate;

wherein the shuttle includes angled slots coupled to the upper endplate with shuttle pins, during axial translation of the shuttle in a proximal direction on the threaded portion of the driver, the shuttle pins translate up the angled slots to lift the proximal end of the upper endplate away from the body to change the lordosis angle.

8. The variable lordosis endplate of claim 7, wherein in the first position the variable lordosis endplate is in a collapsed state with the upper surface of the upper endplate being parallel to the lower surface of the lower endplate.

9. The variable lordosis endplate of claim 7, wherein in the second position the variable lordosis endplate is in an expanded state with a lordosis angle between the upper endplate and the lower body surface.

10. The variable lordosis endplate of claim 7, wherein movement of the shuttle driver from the first position to the second position lifts the proximal end of the upper endplate while rotating the upper endplate away from the lower end plate and changing the lordotic angle of the variable lordosis endplate.

11. The variable lordosis endplate of claim 7, wherein in the first position there is no lordosis angle and in the second position there is a maximum lordosis angle.

12. The variable lordosis endplate of claim 7, wherein the lordosis angle is between 0 to 30 degrees.

13. The variable lordosis endplate of claim 7, wherein the lordosis angle is variable by stopping the translation of the shuttle anywhere between the first and second positions.

14. The variable lordosis endplate of claim 7, wherein rotation of the driver in a distal direction translates the shuttle distally and simultaneously, the shuttle pins are translated downwardly in the angled slots to rotate the upper endplate around the hinge pin to lower the lordotic angle.

* * * * *